United States Patent [19]
Scott et al.

[11] Patent Number: 5,242,373
[45] Date of Patent: Sep. 7, 1993

[54] MEDICAL SEED IMPLANTATION INSTRUMENT

[76] Inventors: Walter P. Scott, 3115 Harbor Dr., St. Augustine, Fla. 32084; Felix W. Mick, 200 California Rd., Bronxville, N.Y. 10708

[21] Appl. No.: 760,986

[22] Filed: Sep. 17, 1991

[51] Int. Cl.⁵ .............................................. A61M 36/00
[52] U.S. Cl. ........................................ 600/7; 128/659; 604/16; 604/93
[58] Field of Search .................................... 600/1–8; 604/60–64, 51, 59, 93, 164, 16–18; 128/654, 655, 659

[56] References Cited

U.S. PATENT DOCUMENTS

| | | | |
|---|---|---|---|
| 4,402,308 | 9/1983 | Scott | 600/7 |
| 4,461,280 | 7/1984 | Baumgartner | 600/7 |
| 4,700,692 | 10/1987 | Baumgartner | 600/7 |

Primary Examiner—Lee S. Cohen
Assistant Examiner—John P. Lacyk
Attorney, Agent, or Firm—Arthur G. Yeager

[57] ABSTRACT

Medical instrument for implantation of radioactive seeds in a body, the instrument including an elongated support rod and an elongated stylet rod spaced apart from and parallel to the support rod, and being held in that relationship by a stop block and a slide block spaced apart from each other and longitudinally slidable with respect to both the support rod and the stylet rod. The stop block is attached to the support rod and the slide block is clampable to each of the support rod and the stylet rod. A seed cartridge with transverse spaced passageways and a central longitudinal through bore receives, stores, and discharges a plug of spaced radioactive seeds by the stylet rod through a connectible hollow elongated implantation needle through which the plug may be implanted in body tissue.

20 Claims, 2 Drawing Sheets

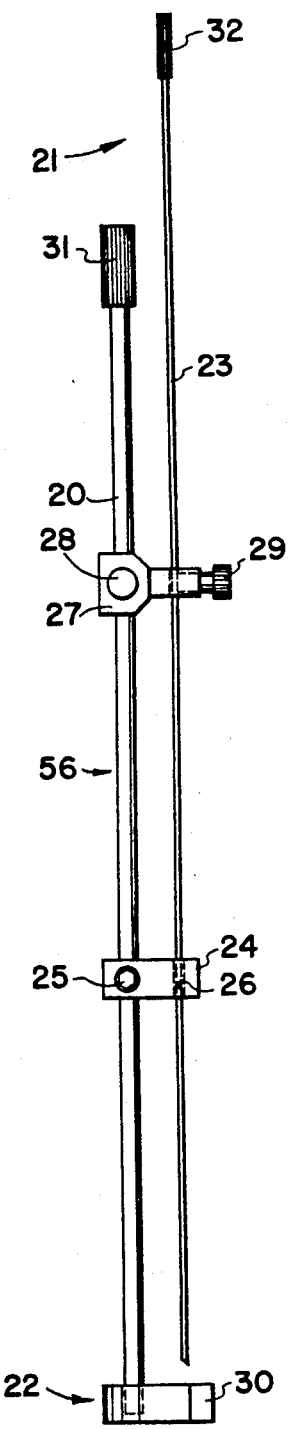
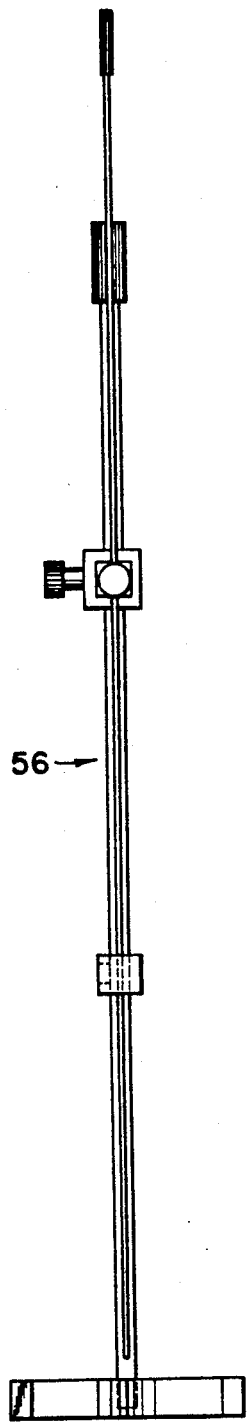
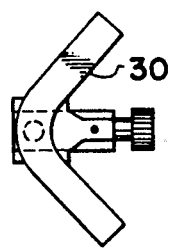
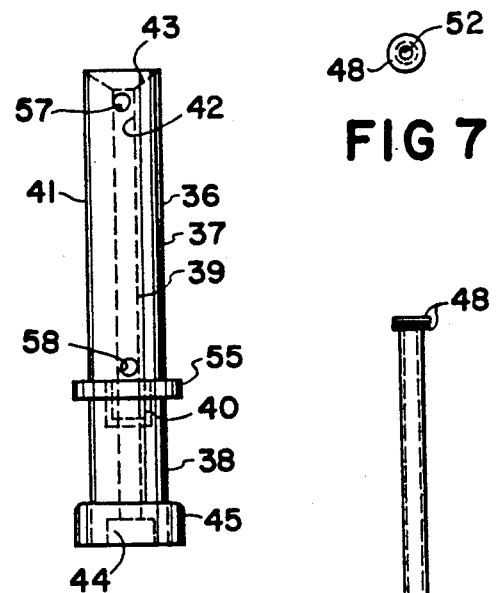
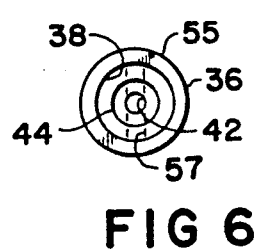
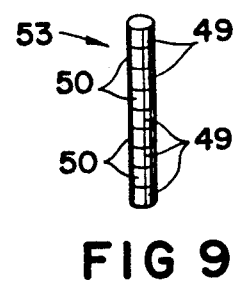
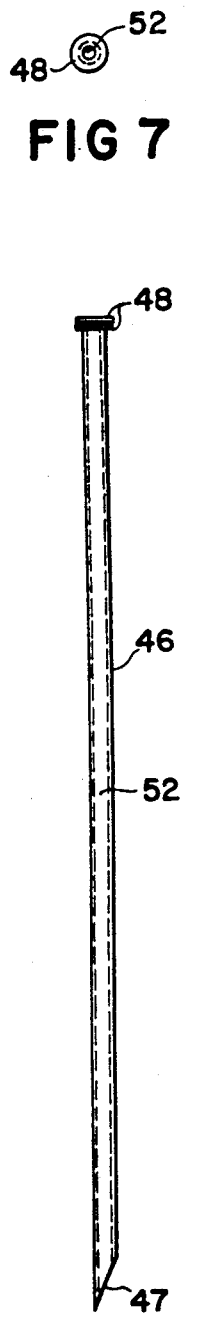
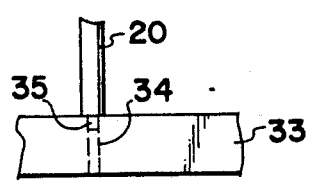

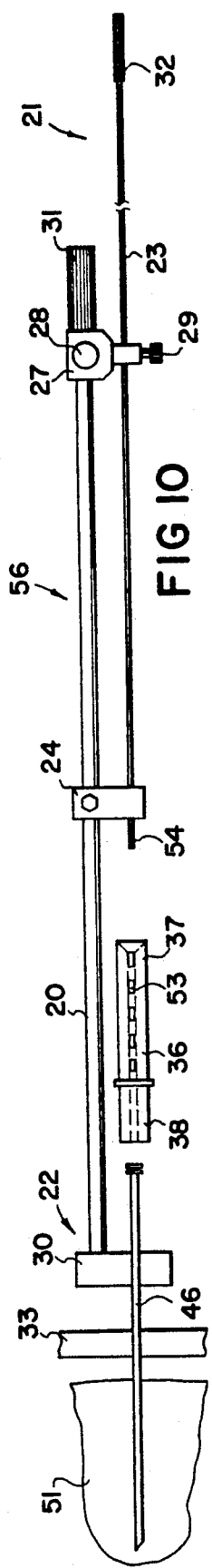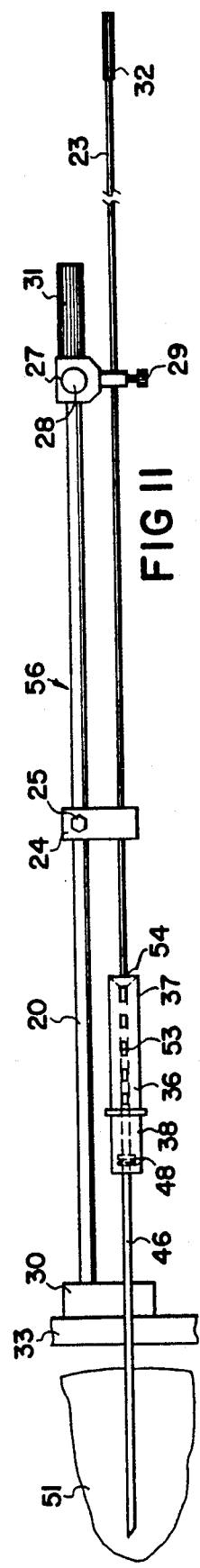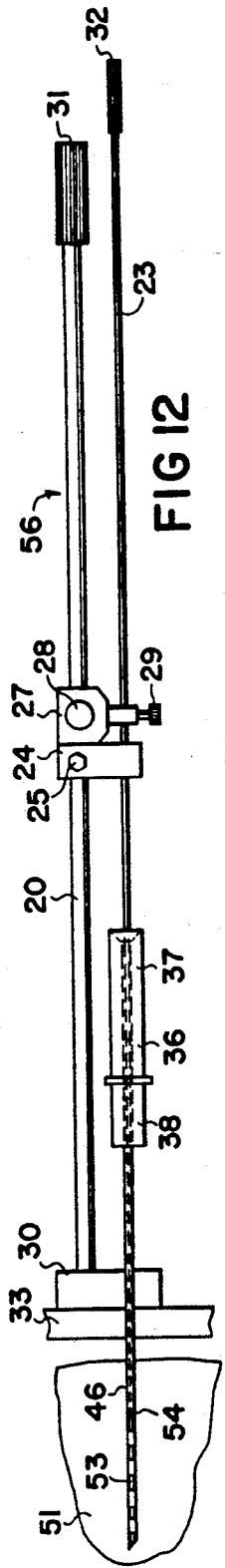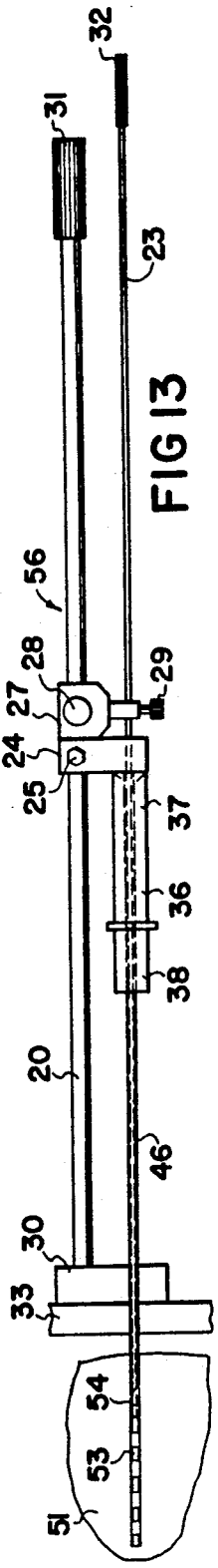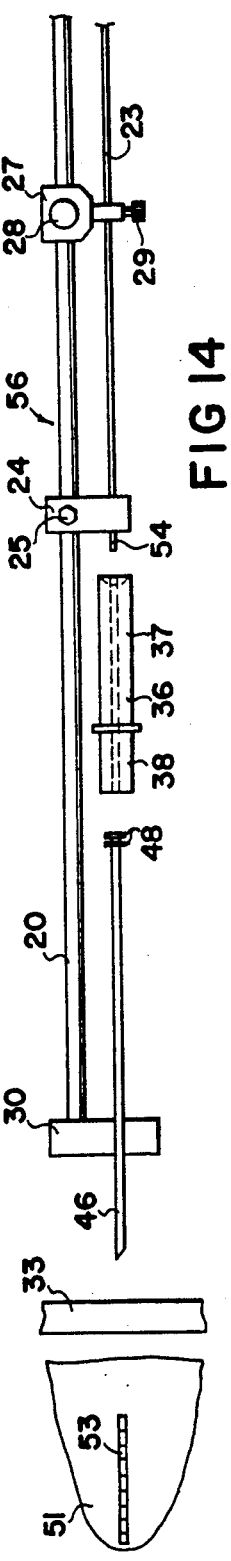

MEDICAL SEED IMPLANTATION INSTRUMENT

BACKGROUND OF THE INVENTION

For many years there has been an established medical technique of controlling the growth of cancer tissue by implanting in that tissue chemical particles (or seeds) of radioactive material that produces radiation which is toxic to cancer tissue. Various chemical isotopes can be employed which have different radiation intensities, and, therefore, different lengths of time over which the radiation occurs before the activity expires. Many of the problems of this medical technique have been solved, but there has remained the problem of how to deliver the seeds to the proper location in the body with precision. It is an object of this invention to provide such a precise delivery instrument. It is another object of this invention to provide an instrument which, for the most part, can be used again and again, by being sterilized after each use, and yet with some parts that may be disposable after a single use. Still other objects will become apparent from the more detailed description which follows.

BRIEF SUMMARY OF THE INVENTION

This invention relates to a radio-active seed implantation instrument including an elongated support rod having distal and proximal ends, and a longitudinal axis. A thin elongated stylet rod is spaced apart from and parallel to the support rod. A stop block is affixed in position on the support rod and slidable with respect to the stylet rod. A slide block is slidable longitudinally along the support rod and the stylet rod and a first clamping means clamps the slide block at any longitudinal position along the support rod and a second clamping means clamps the slide block at any longitudinal position along the stylet rod. A seed cartridge includes a central longitudinal bore for receiving and storing a plug containing a plurality of spaced radio-active seeds, and means for rapid attachment/detachment of the cartridge to a hollow implanatation needle so that the stylet rod may discharge the plug from the cartridge before removal of the needle from the patient thereby leaving the seeds in the patient.

In specific and preferred embodiments of the invention the support rod may be attached to a shoe at its distal end or attached to cooperating medical equipment to stablize the instrument against inadvertent movement. The seed cartridge may be made of stainless steel outer jacket with its inner core of a polyfluorocarbon material. The seed cartridge may include two portions which are joined by screw threads, one portion being the seed carrying portion and the other portion containing a quick coupling mechanism for attachment of the implantation needle thereto. The seed cartridge includes two transverse holes adjaits ends to accept a removable suture which retains the plug during storage and sterilization.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a side elevational view of the stylet rod plunger of this invention;

FIG. 2 is a front elevational view of the stylet rod plunger of this invention;

FIG. 3 is a bottom plan view of the stylet rod plunger of this invention;

FIG. 4 is a partial side elevational view of a second embodiment for stabilizing the stylet rod plunger of this invention;

FIG. 5 is a front elevational view of the seed cartridge of this invention;

FIG. 6 is a bottom plan view of the seed cartridge of this invention;

FIG. 7 is a top plan view of the implantation needle of this invention;

FIG. 8 is a front elevational view of the implantation needle of this invention;

FIG. 9 is a perspective view of the radio-active seed plug of this invention;

FIG. 10 is a side elevational view of the first step in using the instrument of this invention;

FIG. 11 is a side elevational view of the second step in using the instrument of this invention;

FIG. 12 is a side elevational view of the third step in using the instrument of this invention;

FIG. 13 is a side elevational view of the fourth step in using the instrument of this invention; and FIG. 14 is a side elevational view of the fifth step in using the instrument of this invention.

DETAILED DESCRIPTION OF THE INVENTION

The features of this invention are best understood by reference to the attached drawings wherein FIGS. 1-9 illustrate the component parts of the invention and FIGS. 10-14 illustrate the use of the instrument of this invention.

With specific reference to FIGS. 1-9 the instrument has three components; namely, the stylet plunger (FIGS. 1-4); the seed cartridge (FIGS. 5, 6 and 9); and the implantation needle (FIGS. 7 and 8).

The stylet plunger in FIGS. 1-4 includes a support rod 20 and a stylet rod 23 held in spaced parallel relationship to each other by stop block 24 and slide block 27. Support rod 20 is a sturdy inflexible rod or tube, which is employed as an immovable rigid support, while stylet rod is a thin rod or tube which slides lengthwise in its operations. Stop block 24 is located longitudinally along support rod 20 and is affixed thereto. If desired, the stop block 24 may be positioned at any location along support rod 20 by means of a set screw 25 or other equivalent clamping means. Stop block 24 has a passageway 26 therethrough to guide stylet rod 23 but not to be clamped thereto. Slide block 27 also is slidable along support rod 20 and stylet rod 23 and is separately clampable to each. Clamp screw 28 permits slide block 27 to be clamped immovably to support rod 20 and clamp screw 29 permits slide block 27 to be clamped immovably to stylet rod 23. Support rod 20 has an enlarged finger grip 31 at the proximal end 21 of the stylet plunger which also serves as a stop to prevent slide block 27 from sliding over finger grip 31. At the distal end 22 of the stylet plunger support rod 20 is attached a support member in the form of a shoe 30 having a flat bottom surface which can be rested against any other object to stabilize the stylet plunger against lateral or other inadvertent movement since stylet rod 23 must be positioned with some precision to perform in its intended manner. Another embodiment for providing this stability against lateral or inadvertent movement is to attach support rod 20 to a support member in the form of a template 33 by causing the end 35 of support rod 20 to fit snugly into passageway 34 in template 33. Template 33 is a plate with a honeycomb structure which is used to position the implantation needle accurately in the body being treated. Template 33 is not a component part of this invention but is merely a cooperating instrument used in medical seed implantation procedures and as such serves as a solid immovable base for attachment of the style plunger of this invention. Any other cooperating object employed in the medical procedure could also be used as a steady support upon which support rod 20 is attached. The respective positions of stop block 24 and slide block 27 are that slide block 27 should be positioned closer to proximal end 21 and stop block 24 should be positioned closer to distal end 22.

In FIGS. 5 and 6 there is illustrated the seed cartridge 36 employed in this instrument. The purpose for cartridge is to receive, store temporarily, and discharge one or more radio-active seeds into the body tissue at the location desired by the physician or surgeon. Generally, the medical treatment employing this instrument is to control the growth of cancerous tissue, by radiation from the implanted seeds. Normally, a plurality of seeds is implanted in the tissue at spaced intervals, a typical plurality being five (5) seeds. The seeds are solid materials, generally isotopes of chemical elements, such as radioactive iodine, iridium, radon, gold and palladium. The seeds preferably are prepared in the form of a column or plug 53 (see FIG. 9) of five seeds 49 spaced apart from each other by short lengths 50 of absorbable suture, such as No. 3 surgical gut. Each piece of suture may be about 0.5 cm. in length, and each seed about 0.5 cm. in length making the entire plug of 5 seeds being about 4.5–5.0 cm. long. The cartridge 36 of FIGS. 5 and 6 is a generally cylindrical container having a through bore 42 extending axially through cartridge 36 and of a size to receive the plug 53 of FIG. 9, hold plug 53 in cartridge 36, and eventually permit plug 53 to be discharged from cartridge. In a preferred design cartridge 36 has two sections; namely, seed carrying upper section 37 and needle attachment lower section 38, the two sections being joinable through cooperating screw threads 40. Upper section 37 has a funnal shaped entrance 43 to bore 42. Lower section 38 has a flange 55 at its coupling joint to facilitate handling, and a needle coupling recess 44 toward distal end 22 of the instrument. Recess 44 receives the flanged end 48 (see FIGS. 7 and 8) of the implantation needle with a quick coupling means (not shown) at 45, well known in the art. There are several types of quick coupling devices, and any suitable type is operable here. Such types may include spring biased detents, keys and keyways, compressible flanges that snap into a groove, etc.

Preferably, for the sake of handling and sterilization, cartridge 36 is made of a stainless steel outer jacket with an inner core of a polyfluorocarbon such as "Teflon". It is a suitable alternative for the cartridge 36 to be stainless steel, and bore 42 to be merely coated with the polyfluorocarbon, it being important to permit ready sliding of the plug 53 through the bore 42 and to provide a good shield to the radioactive seeds.

In FIGS. 7 and 8 there is shown implantation needle 46 having a sharpened point 47 at its distal end and a flanged proximal end 48, with a longitudinal hollow 52 extending through the complete length of the needle. Hollow 52 is sized to receive plug 53 of seeds 49 and suture spacers 50, and generally is the same size as that of bore 42 in cartridge 36. Flange 48 cooperates with the quick attachment means at 45 in lower section 38 of cartridge 36 to be received and held firm in recess 44. If desired, a different type of needle may be used for needle 46. Namely, an outer sheath and a removable stylet having a trocar point with the quick attachment means 45 at the upper end of the sheath may be employed.

The manner in which the instrument of this invention is used in a medical seed implantation procedure is shown in the sequences of FIGS. 10–14. In FIG. 10 implantation needle 46 has been inserted into the body tissue 51 to the precise depth and location as desired by the physician/surgeon. Normally this is accomplished with the help of instruments embodying ultrasound techniques for directing the insertion of implantation needle 46. Among other components of each ultrasound equipment is a template 33 through which implantation needle is guided. Template 33 is a honeycomb structure with a plurality of passageways therethrough for guiding needle 46. Stylet plunger 56 and seed cartridge 36 loaded with seed plug 53, are near at hand for assembly. In FIG. 11 slide block 27 has been positioned on support rod 20 spaced above stop block 24 and is clamped in place on support rod 20 by tightening clamp screw 28. Cartridge 36 is snap fastened to the flange end 48 of implantation needle 46, shoe 30 is placed firmly against template 33 (or support rod 20 inserted into template 33 as in FIG. 4), and stylet rod 23 is extended so that the distal end 54 touches the upper end of cartridge 36. Stop block 24 has been prepositioned on support rod 20 or pre-clamped in place by set screw 25. The exact location of stop block 24 on support rod 20 is somewhat arbitrarily chosen and may vary depending on the length of support rod 20 and the position of cartridge 36, etc. Stop block 24 must always be above (toward proximal end 21) cartridge 36 because, otherwise, the two components will interfere with each other due to the fact that both are guides to movable stylet rod 23. The critical distance is that between slide block 27 and stop block 24, which as will be described below is the travel of stylet rod 23 in placing plug 53 at the proper position for implantation.

In FIG. 12, clamp screw 29 has also been tightened at its location, as shown in FIG. 11, so as to make stylet rod 23 tightly attached thereto. Clamping screw 28 is then loosened and moved along with stylet rod 23 to contact with stop block 24. This movement causes the distal end 54 of stylet rod 23 to move from its position in FIG. 11 to its position in FIG. 12 causing seed plug 53 to be advanced to the sharp tip 47 of implantation needle 46.

In FIG. 13 seed cartridge is pulled upwardly along stylet rod 23 as a guide until cartridge 36 contacts stop block 24. This movement retracts needle 46 from its original insertion depth to some shallower depth or to complete retraction from the body depending on several other factors, such as the original depth of penetration of needle 46, placement of stop block 24, the length of cartridge 36, etc. In any event the retraction of needle 46 leaves seed plug 53 implanted in the body 51 at the desired location.

In FIG. 14, the entire instrument, including stylet plunger 56, implantation needle 46, and cartridge 36 is removed, disassembled and sent for cleaning and sterilization for subsequent use.

The materials of construction are those for comparable medical instruments, i.e., preferably stainless steel or any other sterilizable rigid metal or plastic. Modern seed cartridges have been made of a combination of lead to protect the user against radiation and acrylic plastic for transparency, but since there have been problems with these cartridges during sterilization, it is preferred to employ stainless steel with polyfluorocarbon cores, as mentioned above.

It is to be appreciated that different persons treated by use of this instrument may require different seeds, different numbers of seeds, and different implantation locations. Accordingly, different locations of stop block 24, slide block 27, cartridge 36, and needle 46 may be required.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A radio-active seed implantation instrument comprising the combination of an elongated support rod having a distal end, a proximal end, and a longitudinal axis, a thin elongated stylet rod spaced apart from and parallel to said support rod, said stylet rod having a distal end, a proximal end, and a longitudinal axis; a stop block positioned longitudinally on said support rod and said stylet rod, a slide block slidable longitudinally along said support rod and said stylet rod and having a first clamping means to clamp said slide block to said support rod at any longitudinal position along said support rod and a second clamping means to clamp said slide block to said stylet rod at any longitudinal position along said stylet rod, a hollow implantation needle having a sharpened distal end and a proximal end, and a seed cartridge having a central bore adapted to receive and store a plug containing a plurality of spaced radio-active seeds, and means for rapid attachment/detachment of said seed cartridge to said proximal end of said implantation needle, said stylet rod being slidable through said central bore of said seed cartridge to move said plug from said cartridge to said distal end of said needle.

2. The instrument of claim 1 wherein said support rod at its distal end has a shoe generally perpendicular to said support rod and adapted to rest against a flat surface to stabilize said instrument.

3. The instrument of claim 1 wherein said distal end of said support rod including means for connections to a medical instrument employed to precisely locate the internal body position for deposition of spaced radio-active seeds adapted to be loaded in said seed cartridge.

4. The instrument of claim 1 wherein said seed cartridge has a proximal portion adapted to contain a plug containing a plurality of spaced radio-active seeds and a distal portion containing said rapid attachment/detachment means.

5. The instrument of claim 4 wherein said seed cartridge portions are coupled together by screw threads in each portion.

6. The instrument of claim 1 wherein said implantation needle includes a flange means at its proximal end adapted to be engaged by said rapid attachment/detachment means in said seed cartridge.

7. The instrument of claim 1 wherein said cartridge has an outer jacket of stainless steel and an inner core of a polyfluorocarbon.

8. A radio-active seed implantation instrument having a proximal end and a distal end and comprising the combination of a stylet plunger and a seed cartridge; said stylet plunger including an elongated support rod and an elongated stylet rod spaced apart from and parallel to said support rod and maintained in that spaced parallel relationship by a stop block and a slide block spaced apart longitudinally on said support rod and said stylet rod respectively, said slide block being located between said stop block and said proximal end of the instrument and having a first clamping means to selectively clamp said slide block to said support rod at any position between said stop block and said proximal end, and having a second clamping means to selectively clamp said slide block to said stylet rod at any position along said stylet rod, and said seed cartridge being a container with a longitudinal through bore adapted to receive and store a plug of spaced radio-active seeds, and said stylet rod and said seed cartridge being positioned such that said stylet rod is slidable through said longitudinal through bore of said seed cartridge.

9. The instrument of claim 8 wherein said cartridge has a stainless steel outer jacket and a core of a polyfluorocarbon.

10. The instrument of claim 8 wherein said support rod includes means adjacent said distal end to stabilize said support rod against lateral movement.

11. The instrument of claim 10 wherein said means to stabilize is a base with a flat support surface attached perpendicular to said rod.

12. The instrument of claim 10 wherein said means to stabilize further include means for attachment of said support rod to an immobile surface of a medical device employed to locate an implantation needle accurately.

13. The instrument of claim 8 wherein said seed cartridge comprise two coupled couplable portions, one of which is the seed carrying portion, and the other of which contains a quick coupling means for attachment of a hollow implantation needle thereto.

14. A medical instrument comprising an elongated support rod having a proximal end and a distal end and an elongated stylet rod maintained in a spaced parallel relationship to each other by means of a stop block and a slide block longitudinally spaced apart from each other, said slide block being slidably mounted on each of said rods, said stop block being located at a predetermined position between said proximal and distal ends of said support rod and being affixed thereto, said stylet rod being slidably mounted to said stop block, said slide block having a first means to clamp said slide block to said support rod at any longitudinal position along said support rod between said stop block and said proximal end, and said slide block having a second means to clamp said slide block to said stylet rod at any longitudinal position along said stylet rod.

15. The instrument of claim 14 which additionally includes a shoe perpendicular to and connected to said distal end of said support rod and having a flat support surface adapted to contact another object and stabilize said support rod against lateral movement.

16. The instrument of claim 14 which additionally includes a support member and means at said distal end of said support rod to rigidly attach said support rod to said support member to stabilize said support rod against lateral movement.

17. The instrument of claim 14 which additionally includes a support member having at least one passageway therethrough, and means at said distal end of said support rod including a reduced projection to fit within said passageway of said support member.

18. A radio-active seed implantation instrument comprising an elongated support rod having a distal end, a proximal end, and a longitudinal axis, a thin elongated stylet rod spaced apart from and parallel to said support rod and having a distal end, a proximal end, and a longitudinal axis, a stop block attached to said support rod and said stylet rod, a slide block slidable longitudinally along said support rod and said stylet rod, a clamping means to clamp in position said slide block to said support rod at any longitudinal position along said support rod between said stop block and said proximal end of said support rod, and another clamping means to clamp in position said slide block to said stylet rod at any longitudinal position along said stylet rod, a plug containing a plurality of spaced radio-active seeds, a seed cartridge having a central bore receiving and storing said plug, an implantation needle having a hollow extending from a sharpened distal end to a proximal end thereof, and means adjacent said proximal end for removably attaching said proximal end of said implantation needle to said seed cartridge, said stylet rod being slidable through said hollow and said central bore to move said plug from said cartridge to said distal end of said needle.

19. The instrument of claim 18 wherein said seed cartridge has a proximal portion containing said plug and a distal portion, said distal portion being removably attached by said means adjacent said proximal end of said implantation needle, and means for releasably securing said proximal and distal end portions of said seed cartridge to inhibit said seeds from inadvertent removal from said seed cartridge.

20. The instrument of claim 18 wherein said seed cartridge includes a pair of spaced lateral bores respectively above and below said plug to receive a stop means for said plug during storage and sterilization of said plug which is removed prior to use of said instrument.

* * * * *